Feb. 26, 1974 B. J. MACHIN Plant Pat. 3,499
CHRYSANTHEMUM PLANT
Filed May 11, 1972
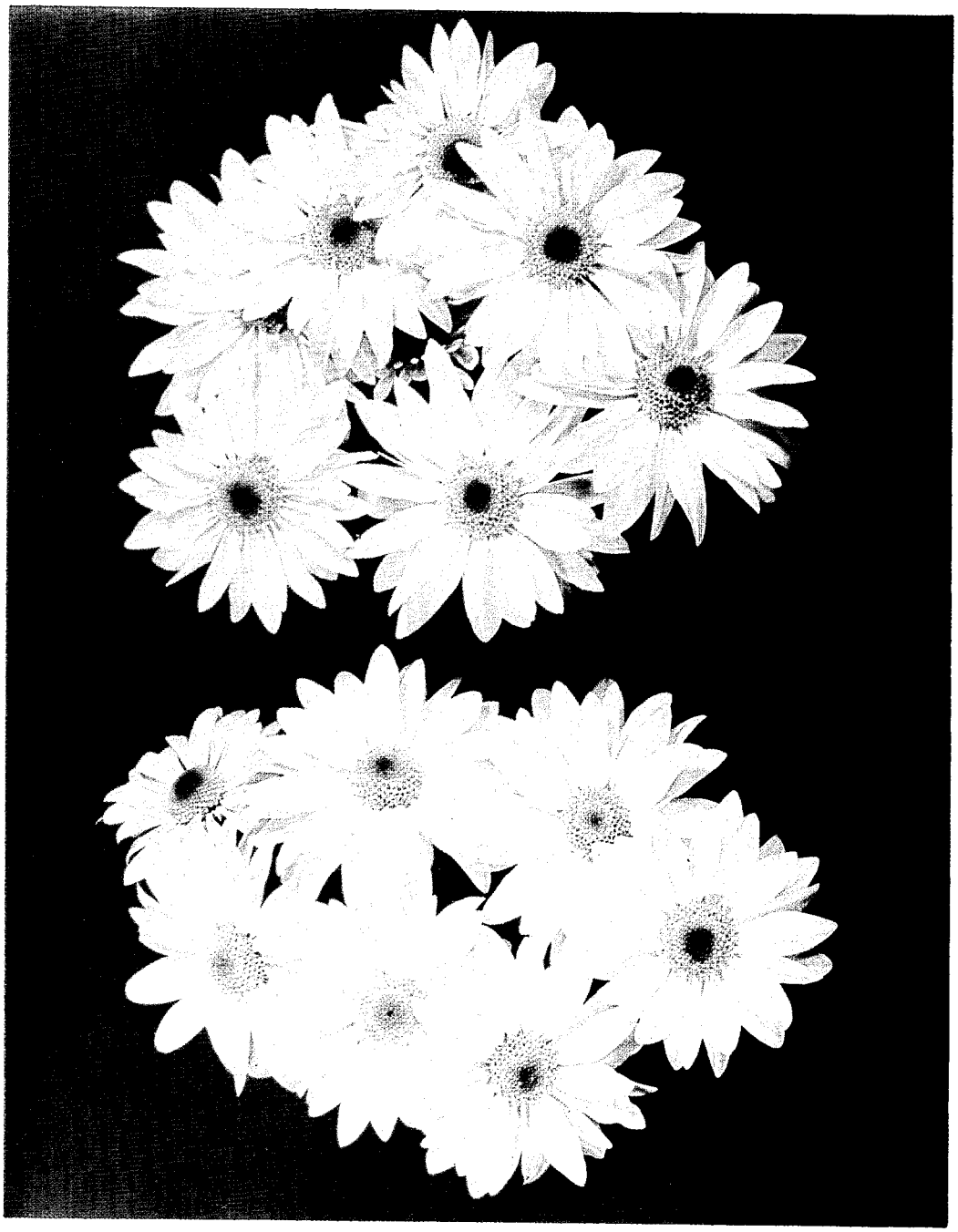

United States Patent Office

Plant Pat. 3,499

Patented Feb. 26, 1974

3,499
CHRYSANTHEMUM PLANT

Barrie J. Machin, Chichester, and G. B. Hall, Ashley Green Chesham, England, assignors to Yoder Brothers, Inc., Barberton, Ohio

Filed May 11, 1972, Ser. No. 252,498
Int. Cl. A01h *5/00*
U.S. Cl. Plt.—74 1 Claim

The present invention comprises a new and distinct cultivar of daisy form chrysanthemum plant which is a sport of the unpatented but commercially well-known cultivar Pink Marble.

The new cultivar is similar in many respects to Florida Marble, disclosed and illustrated in the pending application of Bob G. Coward, filed Feb. 26, 1971, Ser. No. 119,422, now Plant Pat. No. 3,288. The new cultivar has the same characteristics as Florida Marble as:

(1) Flower form.
(2) Plant habit.
(3) Foliage shape.
(4) Recommended period of flowering.
(5) Flowering response.

The new cultivar is distinguished from Florida Marble by the following characteristics, when grown under comparable conditions:

(1) A lighter yellow to off-white flower color.
(2) Flowers approximately ¼ inch smaller in diameter.
(3) Approximately two inches less vigor.

The new cultivar was found in a flowering block of the parent cultivar at Ashley Green Chesham, Buck, England, and when asexually reproduced by cuttings of Chichester, Sussex, England, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the northern and western United States is from April through October; in coastal California, January through December; and in Florida, December through April.

The accompanying drawing shows the unique characteristics of the new cultivar, the color being as nearly true as possible with color photographs of this type. In the drawing, the new cultivar appears on the left and the cultivar Florida Marble on the right.

In the description which follows, color references are made to the Munsell Color Book, 1963 edition, and comparisons are made with the cultivar Florida Marble. Where only a single value or description appears for the new cultivar, the same value or description applies also to the comparison cultivar. It should also be noted that the photograph comprising the application drawing does not clearly bring out the differences in color between the new and comparison cultivar. However, such differences will be apparent from the color values listed below for the respective cultivars.

Botanical classification: *Chrysanthemum morifolium*

| | Polished Marble | Florida Marble |
|---|---|---|
| Bloom: | | |
| Size | 2½″ | 2¾″. |
| Fully expanded | 3″ | 3¼″. |
| Borne | In compound lateral clusters of 5 to 8. | |
| Stems | Wiry | |
| Form | Daisy | |
| Permanence | 7 days | |
| Color: | | |
| Center of flower | Light green, 2.5GY5/8 to dark yellow, 6.25Y8.5/12 | |
| Base of petals | Yellow, 7.5Y8.5/10 | |
| Inside of petals | Yellow, 7.5Y8.5/10 to light yellow, 19Y9/4 | Yellow, 7.5Y8.5/10 to light yellow, 7.5Y9/6. |
| Reverse of petals | do | Yellow, 7.5Y8.5/8 to light yellow, 7.5Y9/6. |
| Tonality from a distance | Very pale yellow to off-white | Yellow. |
| Discoloration | Very pale yellow, 10Y9/4 | Light yellow, 7.5Y9/6. |
| Petals: | | |
| Texture | Smooth | |
| Appearance & form | Open at base, broad at mid-point tapering to a blunt point | |
| Arrangement | Composite, whorled on a single receptacle | |
| Persistence | Resist shatter | |
| Fragrance | Typical chrysanthemum | |
| Reproductive organs: | | |
| Stamen, anthers | 200–250 | |
| Pollen | Abundant to none (functional sterility) | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | Approximately 42″ to 47″ on single stem crops given 3–5 long day weeks and 12–14 weeks total crop time as designated in the tables of Yoder Brothers, Inc., Barberton, Ohio. | Approximately 44″ to 49″ on single stem crops given 3–5 long day weeks and 12–14 weeks total crop time as designated in the timetables of Yoder Brothers, Inc., Barberton, Ohio. |
| Spread | None when grown single stem to moderate when pinched | |
| Foliage: | | |
| Top side | Dark green, 7.5GY3/4 | |
| Size | 5¾″ long, 3¼″ wide | 6″ long, 3 3/16″ wide. |
| Quantity | Numerous | |
| Shape | Spatulate lobed | |
| Texture | Smooth | |
| Ribs & veins | Prominent | |
| Edge | Moderately indented | |
| Serration | Moderate | |
| Under side | Light green, 7.5GY5/4 | |
| Stipules | Prominent | |

We claim:

1. A new and distinct cultivar of daisy form chrysanthemum characterized particularly as to its uniqueness when compared to Florida Marble by its pale yellow to off-white color, it's approximately one-fourth inch smaller flower, and it is approximately two inches less vigor.

No references cited.

ROBERT E. BAGWILL, Primary Examiner

UNITED STATES PATENT OFFICE

CERTIFICATE OF CORRECTION

Patent No. PP-3499 Dated February 26, 1974

Inventor(s) BARRIE J. MACHIN and G. B. HALL

It is certified that error appears in the above-identified patent and that said Letters Patent are hereby corrected as shown below:

In the tabulated description below columns 1 and 2, below "Color" opposite "Inside of petals", under "Polished Marble" change "19Y9/4" to --10Y9/4--.

Signed and sealed this 1st day of October 1974.

(SEAL)
Attest:

McCOY M. GIBSON JR.
Attesting Officer

C. MARSHALL DANN
Commissioner of Patents